United States Patent [19]

Yarger

[11] Patent Number: 5,360,414

[45] Date of Patent: Nov. 1, 1994

[54] TUBE FOR DRAINING BODY CAVITIES, VISCERA AND WOUNDS

[76] Inventor: Richard J. Yarger, 4908 Douglas Dr., Yakima, Wash. 98908

[21] Appl. No.: 959,162

[22] Filed: Oct. 8, 1992

[51] Int. Cl.⁵ .................... A61M 5/00; A61M 25/00
[52] U.S. Cl. .................... 604/264; 604/280; 604/43
[58] Field of Search .................... 604/20, 35–37, 604/41–45, 48, 54, 73, 75, 123, 125, 129, 236, 264, 274, 280, 282, 327, 266; 606/191, 192, 194, 196, 197

[56] References Cited

U.S. PATENT DOCUMENTS

| | | | |
|---|---|---|---|
| 1,226,513 | 5/1917 | Herman . | |
| 2,930,378 | 3/1960 | Buyers . | |
| 3,020,913 | 2/1962 | Heyer . | |
| 3,582,234 | 6/1971 | Isreeli et al. . | |
| 3,599,641 | 8/1971 | Sheridan | 604/256 |
| 3,623,484 | 11/1971 | Schulte . | |
| 3,630,206 | 12/1971 | Gingold . | |
| 3,993,080 | 11/1976 | Loseff . | |
| 4,277,432 | 7/1981 | Woinowski | 264/173 |
| 4,368,739 | 1/1983 | Nelson, Jr. | 604/54 |
| 4,398,910 | 8/1983 | Blake et al. . | |
| 4,431,005 | 2/1984 | McCormick . | |
| 4,445,897 | 5/1984 | Ekbladh et al. | 604/280 |
| 4,459,990 | 7/1984 | Barnea . | |
| 4,465,481 | 8/1984 | Blake | 604/280 |
| 4,531,935 | 7/1985 | Berryessa | 604/45 |
| 4,540,402 | 9/1985 | Aigner | 604/44 |
| 4,543,089 | 9/1985 | Moss | 604/93 |
| 4,573,965 | 3/1986 | Russo | 604/30 |
| 4,573,979 | 3/1986 | Blake | 604/240 |
| 4,607,635 | 8/1986 | Heyden . | |
| 4,650,463 | 3/1987 | LeVeen et al. | 604/43 |
| 4,652,255 | 3/1987 | Martinez | 604/27 |
| 4,676,778 | 6/1987 | Nelson, Jr. | 604/45 |
| 4,717,379 | 1/1988 | Ekholmer | 604/43 |
| 4,810,244 | 3/1989 | Allen | 604/44 |
| 4,867,747 | 9/1989 | Yarger | 604/263 |

FOREIGN PATENT DOCUMENTS 2240026 7/1975 France .

Primary Examiner—C. Fred Rosenbaum
Assistant Examiner—V. Alexander
Attorney, Agent, or Firm—Christensen, O'Connor, Johnson & Kindness

[57] ABSTRACT

A suction tube for removing fluid from a body cavity, viscus or wound. The tube has an elongate tubular section (22) with an exterior surface and an interior surface defining an internal longitudinal passageway (30). The tube has a proximal end portion designed to be connected to a suction source and a distal end portion designed to be inserted into a body cavity, viscus or wound. The tubular section (22) includes a plurality of radially extending, circumferentially spaced elongate portions (25) extending along the length of the tubular section. The portions (25) are configured and spaced so that a longitudinal external lumen (26) is provided between each pair of portions (25). A longitudinal entrance channel (32) couples each external lumen (26) with the region surrounding the tubular section. The channels (32) are configured to allow entry of fluids while substantially preventing entry of debris or living tissue from a body cavity, viscus, or wound. A plurality of spaced holes (28) extend transversely through the tubular body (22) coupling the region surrounding the tubular body with the internal longitudinal passageway (30), wherein each of the transverse holes (28) intersects more than one of the entrance channels (32) and lumens (26).

29 Claims, 9 Drawing Sheets

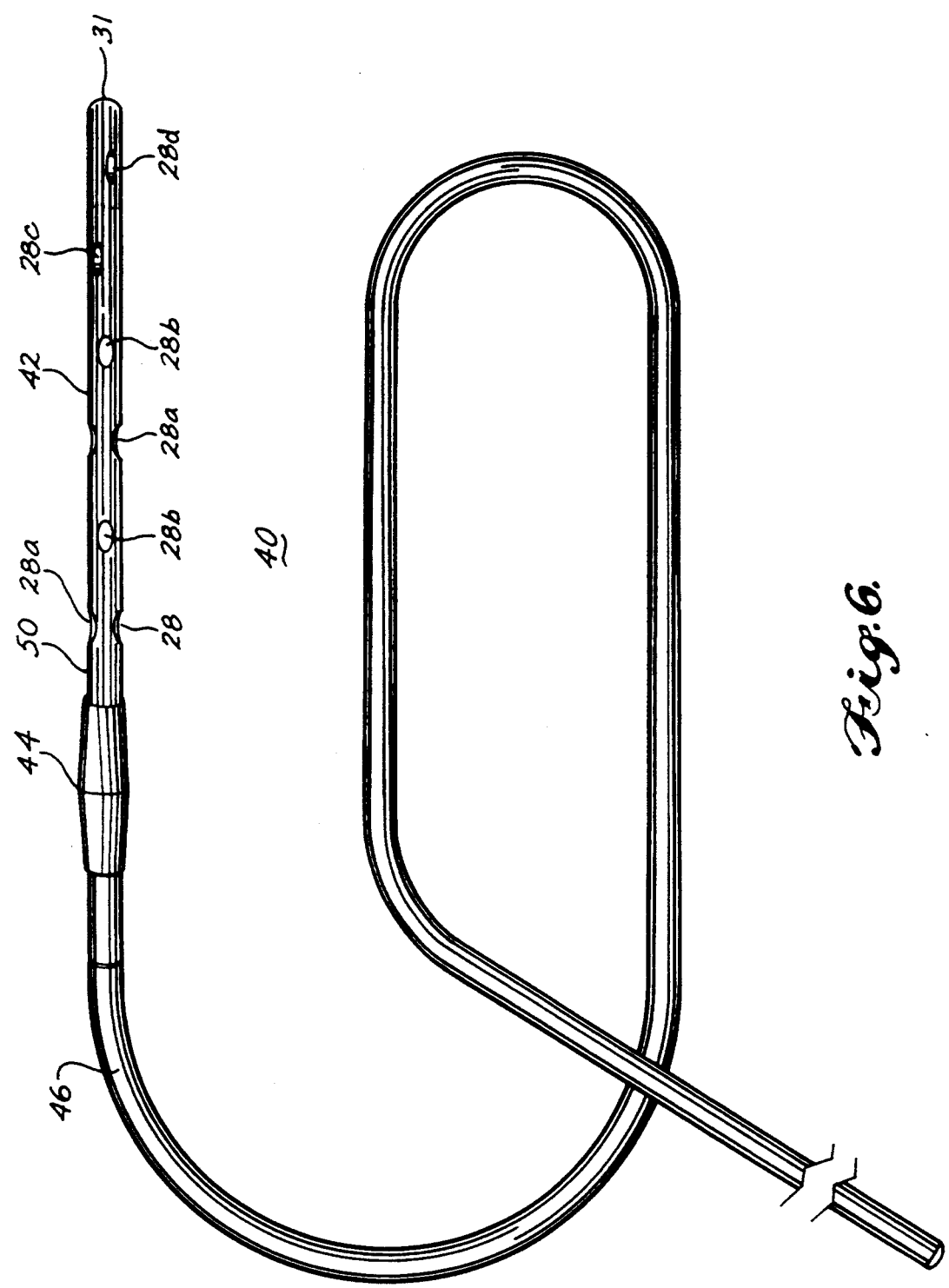

TUBE FOR DRAINING BODY CAVITIES, VISCERA AND WOUNDS

FIELD OF THE INVENTION

The present invention relates to a tube or catheter for draining body cavities, viscera, and wounds.

BACKGROUND OF THE INVENTION

Gastrointestinal functions may not operate properly for various reasons, including illness, disease, treatments involving pain killing drugs or anesthesia associated with a surgical procedure. Air swallowed by the patient can also contribute to gastrointestinal malfunctions because the gas is not efficiently passed through the digestive tract. Abdominal distention can result causing not only bowel function impairment and interference with the absorption of nutrients through the bowel, but also may prevent the patient from breathing deeply or coughing properly, perhaps leading to pulmonary difficulties. Not only does the patient suffer significant pain from abdominal distention, but also with reduced bowel absorption, the patient may become undernourished thereby impeding recovery from disease or surgery.

Various nasogastric aspirator devices have been developed in an effort to avoid abdominal distention. One such device is composed of two different diameter side-by-side tubes, the larger tube having several holes in the distal end for entry of stomach fluids and solids. A suction source is attached to the proximal end of the larger tube. The proximal end of the smaller tube is vented to the atmosphere whereas the distal end of the smaller tube is connected in fluid flow communication with the distal end of the larger tube. This type of nasogastric aspirating device as well as others previously developed often become clogged from stomach phlegm, food or the stomach tissue itself, all of which can block the entrances to the larger aspirator tube or the communicating passage between the smaller and larger tubes. As a result, abdominal distention occurs.

Surgical invasion of a body part generally results in trauma to the part and often an accumulation of body fluids from the tissue itself or from various body fluid systems. In addition, the surgical invasion generally creates a variety of debris, including small portions of tissue and bone, coagulated blood, irrigation fluids, and the like. Normally, it is advantageous to remove such debris and fluids from the surgical site. Accordingly, aspirators and catheters of various types have been developed to remove this material.

A large majority of these wound drain catheters comprise a drain section for fluid communication with the wound and a separate outflow or extension tube for carrying the fluid from the drain section to a reservoir. In some wound drain catheters, the drain section includes a length of tubing that is perforated by forming small apertures through the tubing wall. One significant problem that has been encountered with this type of wound catheter is that the perforations can easily become occluded by the debris remaining from the surgical invasion of the body part. Occlusion can also occur when the body cavity walls collapse around the catheter. When occlusion takes place, it diminishes the efficiency of draining and aspiration or halts it altogether.

Another problem with the perforated wound drainage catheters of the prior art is that living tissue can also be torn away and sucked into the relatively unobstructed perforations, depending upon their size and the degree of suction force used. This can result in additional trauma to the patient and a longer recovery period.

A number of prior art patents disclose wound drain catheters that attempt to solve the above and other problems. Some representative patents in this art are described as follows:

Blake et al., U.S. Pat. No. 4,398,910 and Blake et al., U.S. Pat. No. 4,465,481 disclose wound drain catheters comprised of a fluted drain portion connected by a connector to an outflow tube portion. A preferred embodiment of the drain portion includes a solid core having a longitudinal axis. A plurality of evenly spaced elongated strut portions project radially outward from the core and run along the drain portion. Each strut portion has a generally T-shaped cross section, with the base of the T secured to the core. Each set of adjacent strut portions forms an external lumen that opens through a slot or groove that is formed between adjacent overhand portions of the strut portions. Fluid may be suctioned from a wound through the external lumens traveling the length of the drain portion and entering the outflow portion within a connector.

Ekbladh et al., U.S. Pat. No. 4,445,897, discloses a catheter for draining surgical wounds which includes a hollow catheter tube with a central longitudinal lumen formed therein. One end of the catheter is designed to be connected to a suction source. Two longitudinally extending and diametrically opposed slots are formed in the outer wall of the tip or distal end portion of the tube. The slots widen inwardly to form two external lumens. A plurality of through openings in the base of the external lumens place the external lumens in fluid communication with the inner lumen.

LeVeen et al., U.S. Pat. No. 4,650,463 discloses perforated tubing for use in surgical drains. In the preferred embodiment, a tube body includes a central lumen having a cloverleaf shape cross section. The outer cross-sectional perimeter of the tube conforms to this cloverleaf cross section. Each set of adjacent cloverleaf portions of the tube define an external longitudinal lumen groove. The external lumen grooves open through elongated slots. A plurality of perforations are formed in the bottoms of the longitudinal lumen grooves and place the grooves in fluid flow communication with the central lumen.

U.S. Pat. Nos. 2,930,378, 3,020,913, 4,531,935, 4,543,089 and 4,573,965 disclose a variety of hollow tubular sections with radial openings formed therein for placing the exterior of a tube in fluid communication with an internal lumen formed therein.

In spite of the above approaches to providing catheters or aspirators for draining body cavities, viscera, and wounds, there has remained a need for new and improved methods for such drainage, particularly methods which minimize or eliminate the problem of occlusion of perforations in a tube by debris in a wound or intact living tissue in a body cavity or viscus during drainage or aspiration.

SUMMARY OF THE INVENTION

Accordingly, it is an object of the present invention to provide a suction tube for removing fluid from a body cavity, viscus, or wound, which tube has a central bore and a plurality of holes or openings coupling the bore with the region surrounding the tube, wherein the holes are protected from occlusion by debris or living tissue.

It is another object of the present invention to provide a suction tube having a new and different arrangement of lumens external to the central bore and perforations connecting the lumens to the central bore, at the distal end portion of the suction tube to provide a sumping action to efficiently remove fluids from a body cavity, viscus, or wound.

These and other objects of the present invention, as will hereinafter become more readily apparent, have been achieved by providing a suction tube made up of an elongate tubular body having an exterior surface, an interior surface which defines an internal longitudinal passageway, a rearward or proximal end portion designed to be connected to a suction means, and a forward or distal tip end portion designed to be inserted into a body cavity, viscus, or wound. A plurality of radial portions are attached to, or are integral with, the exterior surface of the tubular body and extend along the length of the tubular body. These portions are configured and circumferentially spaced so that an external lumen and entrance channel is provided between each pair of portions. The entrance channels are configured to allow entry into the lumens of fluid from the region surrounding the tubular body while preventing entry of tissue and debris from a body cavity, viscus, or wound. The lumens communicate with the channels but not normally with the internal longitudinal passageway. However, at the distal end portion of the suction tube, a plurality of spaced holes extend through the tubular body and adjacent entrance channels and external lumens so as to couple the internal longitudinal passageway with the region surrounding the tubular body in fluid flow communication therebetween. In one embodiment, described in greater detail hereinbelow, the suction tube is provided with radio-opaque material affixed to or contained in the tubular body enabling the position of the tube to be monitored when it is inserted in a body cavity, viscus, or wound.

BRIEF DESCRIPTION OF THE DRAWINGS

Other objects and many of the attendant advantages of this invention will be readily appreciated as the same becomes better understood with reference to the following detailed description when considered in connection with the accompanying drawings, in which like reference characters designate the same or similar parts throughout the figures thereof and wherein:

FIG. 6 is a plan view of a second embodiment of the present invention comprising a perforated wound drainage suction tube attached to an outflow tube;

DETAILED DESCRIPTION OF THE PREFERRED EMBODIMENT

Figure 1:
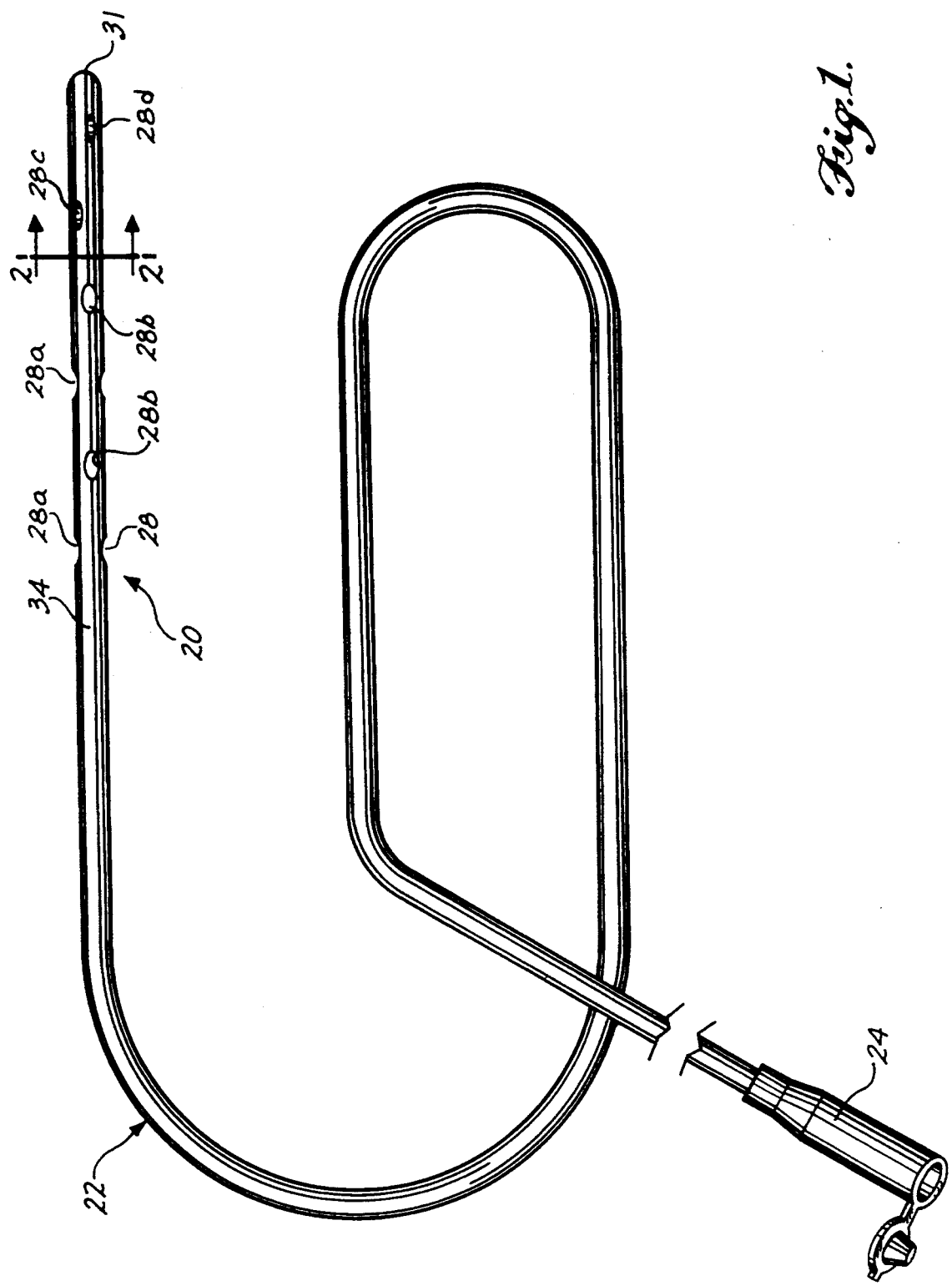
FIG. 1 is a plan view of a preferred embodiment of a nasogastric sumping tube of the invention.

Referring now to the drawings, FIGS. 1–5B show a first preferred embodiment of the present invention, and FIGS. 6–14 show a second preferred embodiment of the present invention. In the first embodiment, shown in FIG. 1, a sump suction tube assembly 20 includes a perforated, elongate tubular section 22 designed to be inserted into the body, for example, through the nose, down the throat, and into a hollow viscus, e.g., the stomach, for removing fluids therefrom, for instance, if the patient's intestines are not functioning properly. As shown in FIG. 1, a connector 24 is engaged around the open, proximal end of the tubular section 22. A vacuum source may be attached to the connector 24.

Referring to FIGS. 1–5, the elongate tubular section 22 defines an interior passageway or bore 30 and includes a plurality of radially projecting portions 25 that extend along the length of the exterior of the tubular section. Typically, projecting portions 25 are integral with tubular section 22, although alternatively the portions may be attached to the exterior surface of the tubular section. Preferably, projecting portions 25 when viewed in cross section (see FIGS. 2, 4 and 5), have a radially extending web section 25a and a transverse exterior flange section 25b, although the specific cross-sectional configuration of portions 25 may vary somewhat from that shown in the Figures. Each projecting portion 25 is configured and circumferentially spaced from adjacent projecting portions such that external lumens 26 are defined between adjacent projecting portions extending along the length of tubular section 22. The external lumens 26 communicate with the region surrounding the tubular section 22 through longitudinal entrance channels 32 that are substantially narrower in width than the widest cross-sectional width of the lumens 26. The entrance channels 32 are sufficiently narrow to prevent significant occlusion of the external lumens by debris or living tissue during drainage. In this regard, preferably the width of the entrance channels 32 may range from 0.1 mm to 1.0 mm, depending on the type of tissue and debris desired to be excluded, the overall diameter of the tube section, and also the volume of the wound to be drained.

The desired diameter of the tubular section and desired flexibility thereof likely will necessitate a particular wall thickness for the tube section, which in turn may affect the thicknesses of web sections 25a and flange sections 25b, and thus, also affect the width of channels 32. Generally, the goal would be to form the inside diameter of the tube section as large as possible, the wall thickness thereof as thin as possible, and the channel width as narrow as possible, while still providing sufficient structural support for the projecting portions. As a further consideration, the combined cross-sectional area of the lumens 26 should bear an appropriate relationship with the cross-sectional area of the bore 30 so that a continuous sumping action is achieved through the use of the present invention. If the cross-sectional area of the bore 30 is relatively too large or relatively too small in relationship to the combined cross-sectional area of the lumens 26, the suction at entrance channels 32 and holes 28 (discussed more fully below) may be too strong or too weak to provide proper sumping at the body site from which it is desired to remove fluids.

Although tubular section 22 has been described as including radially projecting sections 25, the tubular section may alternatively be considered as a tubular member having a relatively thick wall in which a plurality of external lumens 26 and entrance channels 32 are formed.

Figure 2:
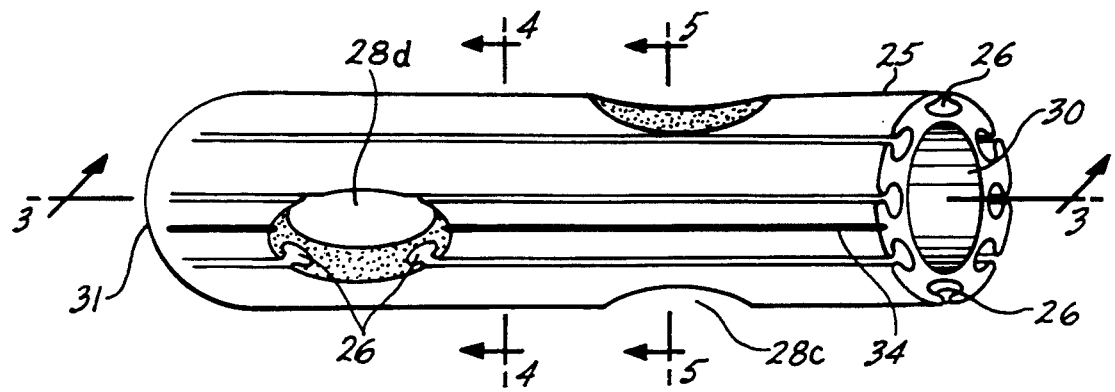
FIG. 2 is a perspective view of the front (distal) end of the device illustrated in FIG. 1.
Figure 3:
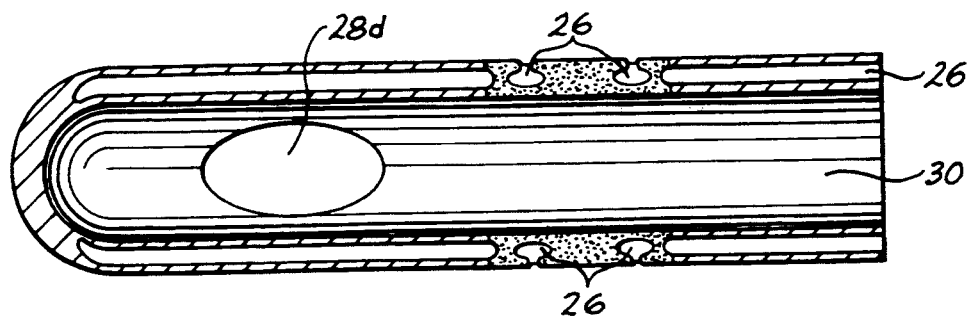
FIG. 3 is a cross-sectional view of the front end of the device shown in FIG. 2, taken along the line 3—3 and looking in the direction of the arrows.
Figure 4:
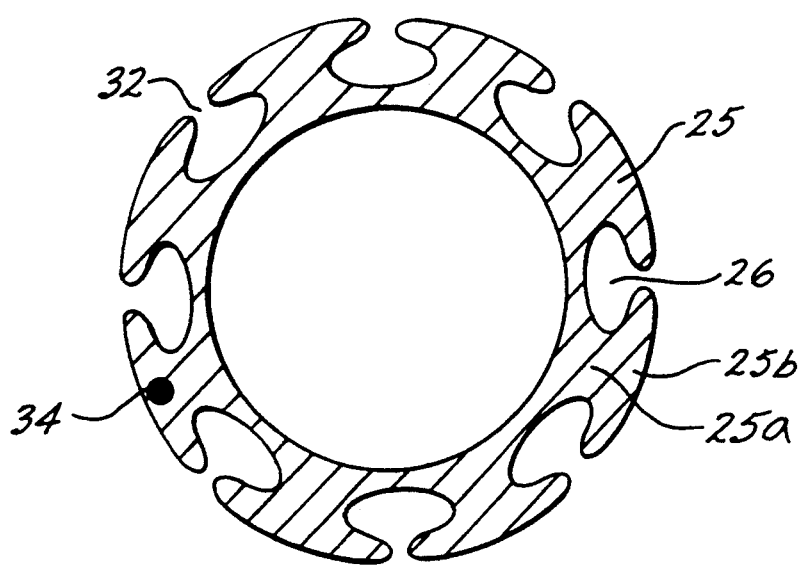
FIG. 4 is a cross-sectional view of the front end of the device shown in FIG. 2, taken along the line 4—4 and looking in the direction of the arrows.

Tubular section 22 includes a plurality of spaced apart transverse holes, generally designated as 28, coupling the hollow interior (longitudinal bore) 30 of the tubular section 22 with the region surrounding the tubular section. Holes 28 are preferably spaced along and around the distal portion of the tubular section 22, remote from the connector 24. The distal tip end 31 of the tubular section 22 is shown as rounded and sealed in the embodiment in FIGS. 1 and 2. Preferably, holes 28 are sufficient in number and are positioned so that each of the holes 28 intersects and is coupled in fluid flow communication with at least one external lumen 26 and entrance channel 32. As seen in FIG. 2, in the illustrated embodiment of the invention, holes 28 are sized and positioned so that each hole is coupled in fluid flow communication with two lumens 26. The number of external lumens and entrance channels intersected by a given hole 28 will depend on the size of the holes and widths of the external lumens and entrance channels, which in turn will depend at least in part on the inside diameter 30 of the tube section 22. Also, ideally the holes 28 are of sufficient number and are positioned so that each lumen intersects at least one of the holes.

Also, preferably the holes 28 are of specific relationship to each other. As shown in FIG. 1, the holes 28a, 28b, 28c and 28d are each in opposed sets which derives from the fact that in the production of the present invention, the tool used to form the holes 28a–28d extends diametrically through the tubular section 22. Also as shown in FIG. 1, the hole set 28a (composed of two diametrically opposed holes) are located 90° from the holes 28b about the longitudinal central axis of the tubular section 22. The hole sets 28a and 28b are repeated at further distal locations as shown in FIG. 1. Further as shown in FIG. 1, the distal most hole sets 28c and 28d are positioned normally (90°) to each other, and also are positioned 45° from the holes 28 and 28b. Further, the external lumens 26 intersecting with holes 28c do not intersect with any of the other sets of holes, i.e., 28a, 28b, or 28d, and the lumens 26 that intersect with holes 28d do not intersect with any of the other sets of holes, i.e., holes 28a, 28b, or 28c. Thus, even if the more proximally located holes 28a and 28b become occluded by body tissue, debris or other matter, continuous sumping action can still occur through the distal most holes 28c and 28d, as discussed more fully below.

Figure 5:
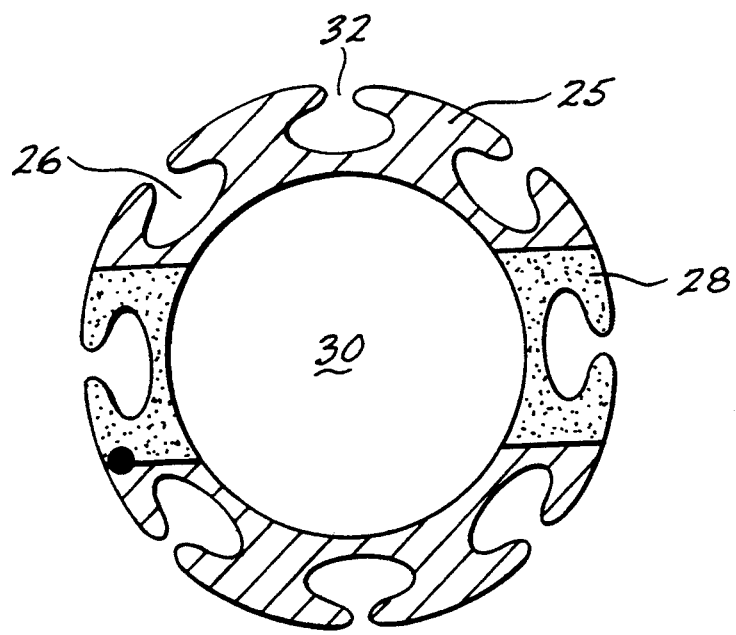
FIG. 5 is a cross-sectional view of the front end of the device shown in FIG. 2, taken along the line 5—5 and looking in the direction of the arrows.
Figure 5A:
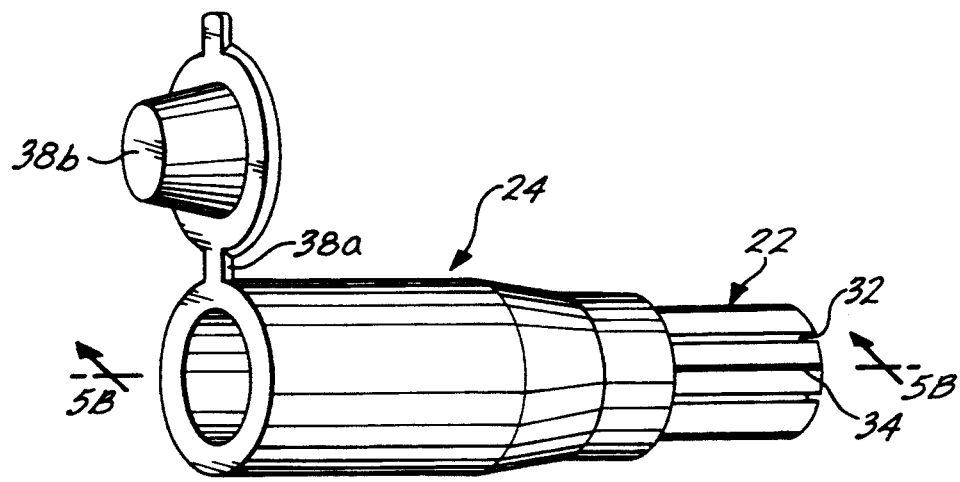
FIG. 5A is a perspective view of the proximal or rear end of the device illustrated in FIG. 1.

In another design criteria, it is important that the diameter of the holes 28 is smaller than the inside diameter 30 of the tubular section 22 so that any debris that does enter the tubular section through the holes 28 will freely travel along the tubular section toward the proximal end thereof:

As shown in FIG. 5A, a connector 24 is engaged over the proximal end of the tubular section 22. The connector 24 has a counterbore 35 for snuggly receiving the proximal end portion of the tubular section 22. The bottom of tile counterbore 35 defines an abutment shoulder 36 against which the proximal end 37 of the tubular section 22 abuts to close off the lumens 26 but not the interior bore 30 of the tubular section 22. As such, at the proximal end of the tubular section 22, the lumens 26 are not in fluid flow communication with the interior 30 of the suction kit section 22 or the interior of the connector 24. Ideally, at the location of shoulder 36, the inside diameter of the connector 24 closely corresponds to the inside diameter 30 of the tube section 22. In the proximal direction from shoulder 36, the interior diameter of the connector 24 is enlarged for reception of a tubular filling, not shown, associated with a vacuum source, not shown. An integral cap 38 may be used to close off the proximal end of the connector 24 when the suction tube assembly 20 is not in use. A thin flexible bridge portion 38a connects the cap 38 to the body of the connector 24. The cap 38 has a plug portion 38b that tits snuggly within the adjacent interior of connector.

In use, the sump section tube assembly 20 is inserted into the body, for example, through the nose, down the throat and into the stomach. When thusly inserted, the distal portion of the tubular section 22, in which the holes 28 are located, is positioned within the stomach for removing fluids and other matter therefrom. It will be appreciated that a substantial portion of the tubular section 22, although located within the body, is not within the stomach per se. Moreover, at least a part of the proximal portion of the tubular section 22 is located outside of the patient's body.

Body fluid may be drawn into the interior 30 of the tubular section 22 directly through holes 28 by a vacuum source (not shown) coupled with connector 24. Not infrequently, the organ walls or body tissue, e.g., interior stomach lining, may collapse around the holes 28 thus closing them off. This is a common problem with known nasogastric suction tubes. However, with the present invention, the body fluid may also enter into the exterior lumens 26 through the entrance channels 32 anywhere along the length of the channels and then travel along the lumens until reaching one of the holes 28 whereupon the fluid can enter the interior 30 of the tubular section 22. The entrance channels 32 are sufficiently narrow to prevent the stomach lining or other tissue, and debris, from entering the lumens. Thus, the lumens will not be closed off by body tissue or debris.

Another advantage of the nasogastric suction tube of the present invention is that fluids may pass into the lumens 26 through the external channels 32 at any location along the lumens, whether at a location external to the body, internal to the body but external to the cavity or viscus being drained or proximal to the suction site, e.g., the stomach, and then travel distally through the lumens until reaching a cross hole 28, and thereupon enter into the interior 30 of the tubular section 22. Fluids, including atmospheric air outside of the body, that enter the tureens will be directed towards a cross hole 28 and into the interior 30 of the tubular section. This provides a continuous sumping action. As such, tissue located adjacent to holes 28 will not tend to be sucked into the holes 28 by a negative pressure at the holes created by the suction source. Accordingly, there is a reduced likelihood that the tissue will cause occlusion of the holes 28. In this regard, the present invention provides a significant advancement over the prior art.

A bead or thin strip 34 of radio-opaque material may optionally be provided extending along the tubular section 22 so that the position of the tube within the body may be monitored by standard techniques. Any standard radio-opaque material may be incorporated, such as barium sulfate.

A second embodiment of the invention is shown in FIGS. 6–15. The suction tube assembly 40 shown in these Figures is configured as a wound drainage sump suction tube. The perforated suction tube 42, which is similar in construction to the tube 22 shown in FIGS. 1–5B, is shown connected to an outflow tube 46. The suction tube 42 is inserted into the wound, operative site, or body cavity, and may remain in place upon closure of the site for draining the site during the recovery period. The suction tube assembly 40 also includes a connector 44 for connecting the suction tube 42 to the longitudinal outflow tube 46 which in turn is connectable to a vacuum source. Typically, the vacuum source is a combination suction and drainage collection device. One example of such devices is a squeeze bulb, not shown, which is collapsed by squeezing to create a suction in the tube assembly 40. As the squeeze bulb is filled, it expands until no further suction is present. At that point, the squeeze bulb may be conveniently emptied. The type of suction/collection device is not intended to constitute the present invention per se.

Figure 7:
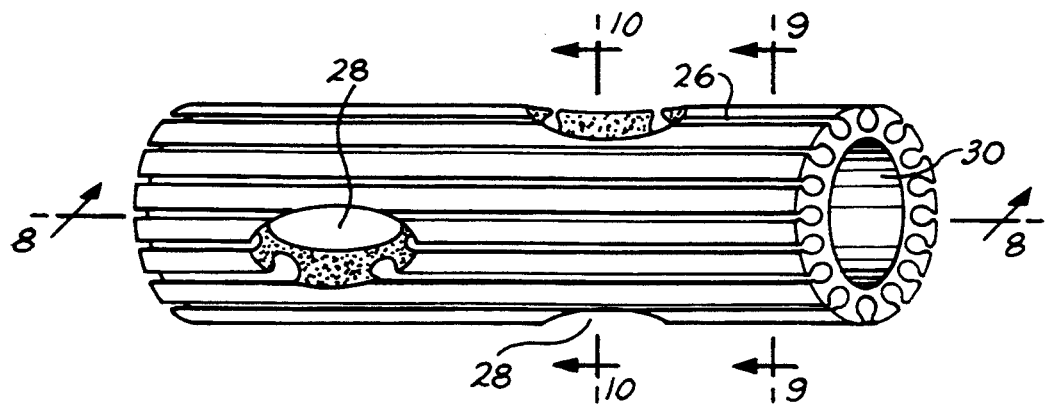
FIG. 7 is a perspective view of a portion of the suction tube illustrated in FIG. 6.
Figure 8:
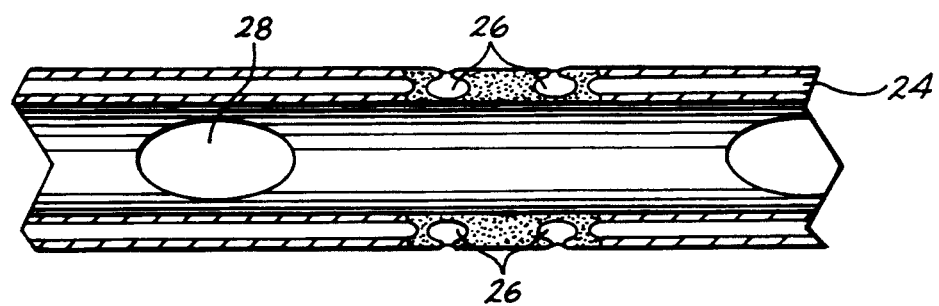
FIG. 8 is a cross-sectional view of the portion of the tube illustrated in FIG. 7, taken along the line 8—8 and looking in the direction of the arrows.
Figure 9:
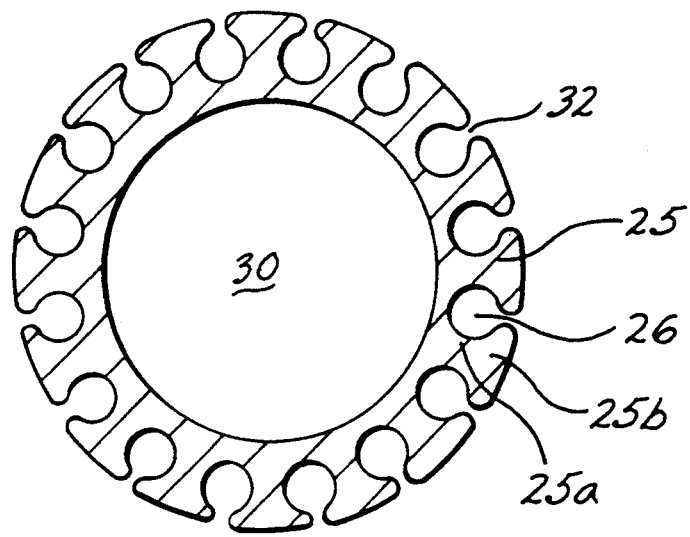
FIG. 9 is a cross-sectional view of the portion of the tube illustrated in FIG. 7 taken along the line 9—9 and looking in the direction of the arrows.
Figure 10:
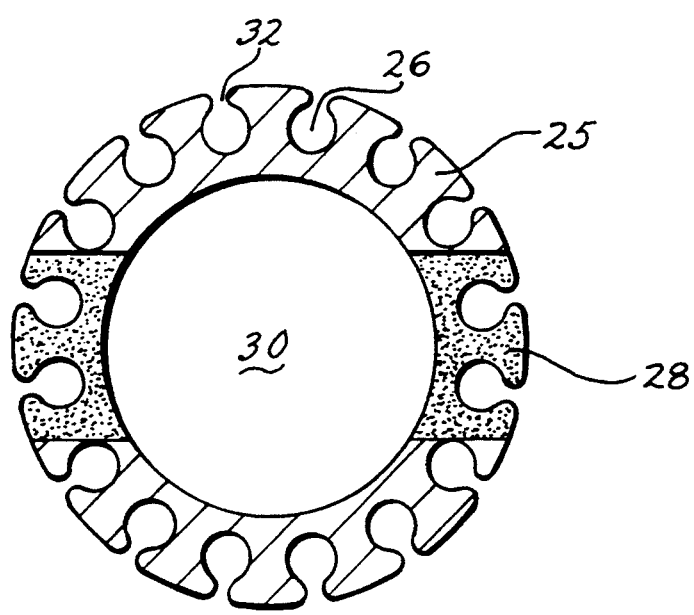
FIG. 10 is a cross-sectional view of the portion of the tube illustrated in FIG. 7, taken along the line 10—10 and looking in the direction of the arrows.
Figure 11:
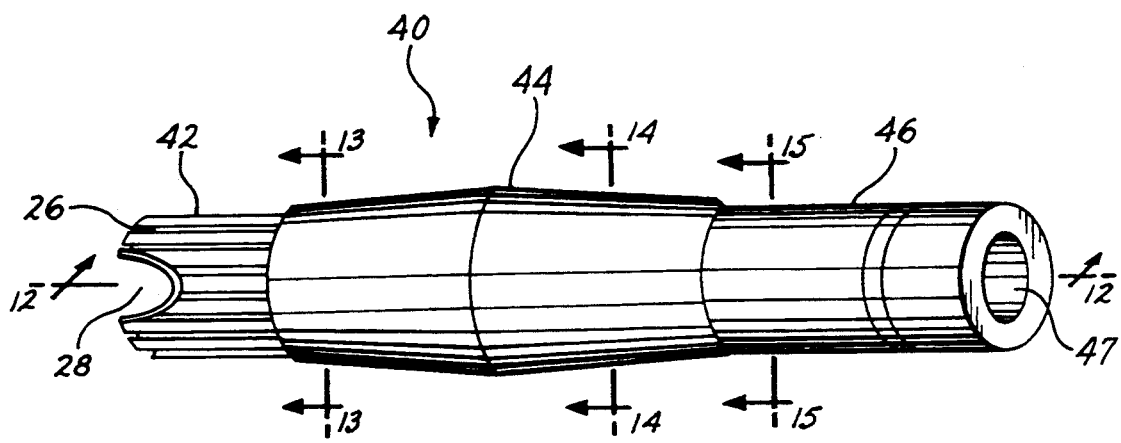
FIG. 11 is an enlarged perspective view of the device shown in FIG. 6 depicting the connection between the perforated suction tube and the outflow tube that is connectable to a vacuum source.
Figure 12:
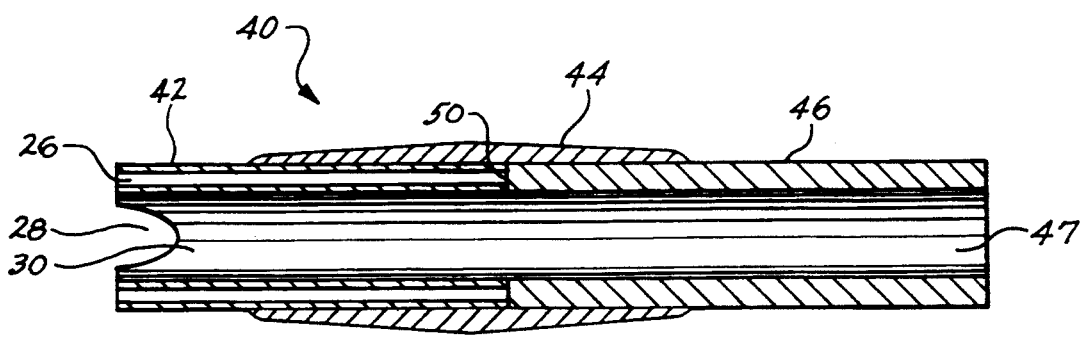
FIG. 12 is a cross-sectional view of the apparatus illustrated in FIG. 11, taken along the line 12—12 and looking in the direction of the arrows.
Figure 13:
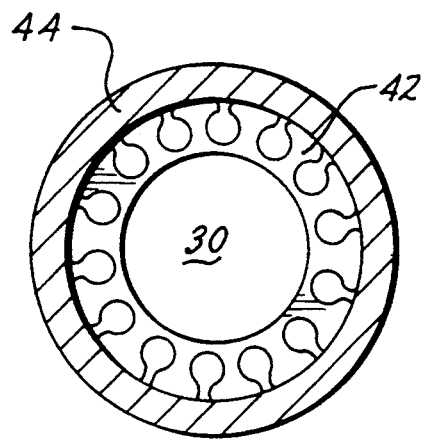
FIG. 13 is a cross-sectional view of the portion of the device shown in FIG. 11, taken along the line 13—13 and looking in the direction of the arrows.
Figure 14:
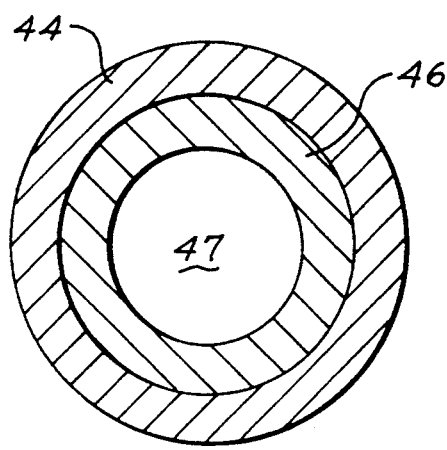
FIG. 14 is a cross-sectional view of the portion of the device shown in FIG. 11, taken along the line 14—14 and looking in the direction of the arrows.

FIGS. 7–10 illustrate a section of the suction tube 42, which is constructed in a manner similar to the perforated portion of tubular section 22 shown in FIGS. 1–5B. Accordingly, the same part numbers for the suction tube 42 are utilized in FIGS. 7–10 as shown in FIGS. 2–5 for the tubular section 22. As seen in FIG. 7, in the illustrated embodiment of the invention, holes 28 are sized and positioned so that each hole is coupled in fluid flow communication with three lumens 26.

Figure 5B:
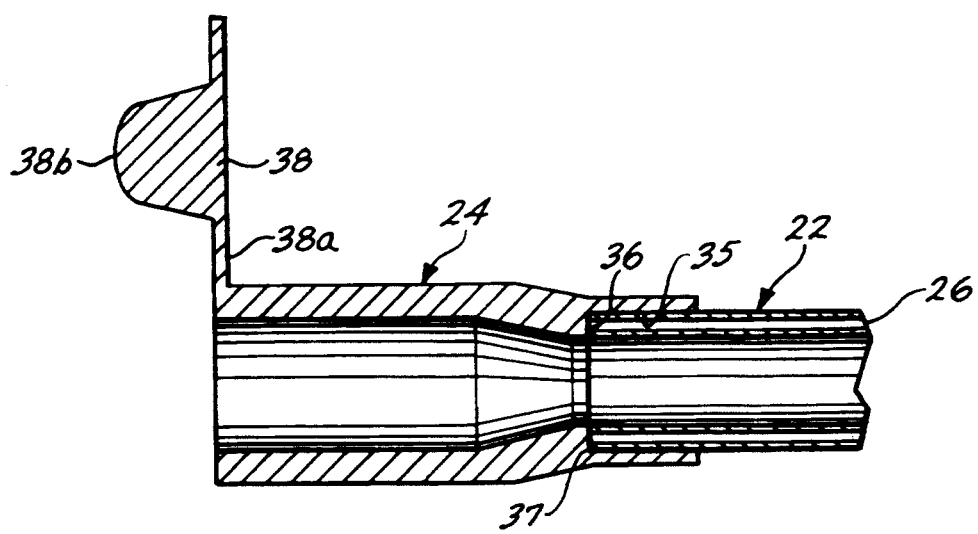
FIG. 5B is a cross-sectional view of the proximal end of the device illustrated in FIG. 5A, taken along the line 5B—5B and looking in the direction of the arrows.
Figure 15:
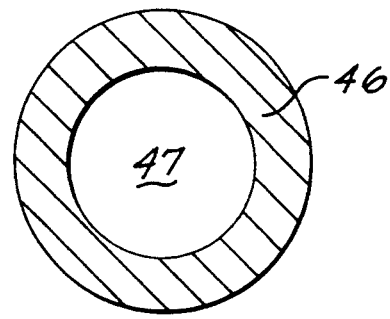
FIG. 15 is a cross-sectional view of the portion of the device shown in FIG. 11 taken along the line 15—15 and looking in the direction of the arrows.

The proximal end 50 of the section tube 42 is positioned within the connector 44 in a manner similar to the interconnection between the proximal end of the tubular section 22 with the connector 24 shown in FIGS. 5A and 5B. In this regard, as shown in FIGS. 11–15, the proximal end 50 of the section tube 42 abuts directly against the distal end of the outflow tube 46 so that the proximal ends of the lumens 26 are closed off by the adjacent end of the outflow tube 46. As such, at the proximal end of the tubular section 22, the lumens 26 are not in fluid flow communication with the interior 30 of the tubular section 42 or the interior 47 of the outflow tube 46. FIGS. 1314 15 show cross-sectional views along various portions of the segment of the suction tube assembly shown in FIG. 11.

The tube assembly 40 is operated in a manner analogous to tube assembly 20 in that the body fluids may enter the interior 30 of the tube 42 directly through holes 28 and also initially into lumens 26 via entrance channels 32, anywhere along the length of the suction tube 42 and then into the holes 28.

The choice of materials for construction of the tubing and other segments of the present invention will depend in part on the intended application. Generally, materials which are nonreactive with body fluids and tissue, that is, bio-inert materials, will advantageously be chosen. Typically, the suction tubes of the invention will be formed of a semi-rigid, resiliently-deformable material, such as an elastomer, suitable for medical use. One type of elastomeric material that may be used is a silicone polymer. In some applications, where the tubing must be inserted lengthwise through a viscus or a body cavity, tile tubing should be formed of somewhat stiffer material, such as vinyl or urethane polymers.

The elongate tubular section 22 may also be made of a transparent or translucent material so that a doctor or nurse can view the flow of fluid through the exterior lumens 26 or the interior 30 of the tube 22.

While tile present invention has been described in terms of a nasogastric suction tube, a body cavity suction tube and a wound drainage tube, it is contemplated herein that the tubes may be used in any body cavity, viscus, wound, or surgical site where removal of fluids, whether liquid or gas, is desired. The fluids may either be those naturally produced by the body, those produced as a result of trauma, or those introduced into the body, such as, for example, irrigation fluids used during surgery.

The tubes may conveniently be provided in sterile condition in a sterilized container.

The cross section of the suction tubes of the present invention can be any of a variety of shapes, and may have one type of cross section, or a combination of different-shaped cross sections, as desired. For instance, the cross sectional shape of the suction tubes may be circular, oval, elliptical, polygonal, (square, rectangular, triangular etc.), etc.

In some embodiments, it may be advantageous to provide fluids to a site rather than remove fluids from the site. However, the most significant advantages of the devices of the present invention are expected to be encountered when the device is used to remove fluids from a site.

Many modifications and variations on the present invention are possible in light of the above teachings. It is therefore to be understood that within the scope of the appended claims, the invention may be practiced otherwise than as specifically described.

The embodiments of the invention in which an exclusive property or privilege is claimed are defined as follows:

1. A suction tube for removing fluids from within a body through a suction source comprising:
   an elongate tubular section having an exterior surface and an interior surface defining an internal longitudinal passageway through the tubular section, the tubular section having a proximal end portion designed to be connected to the suction source and a distal end portion designed to be inserted into the body, wherein the tubular section has a sufficient length such that the proximal end portion is located outside of the body;

a plurality of projecting portions projecting from the exterior of the tubular section, the projecting portions having outer surfaces and being configured and mutually circumferentially spaced about the tubular section so as to form a longitudinal lumen between adjacent ones of the projecting portions, the projecting portions spanning between the distal and proximal end portions of the tubular section so that the lumens span between the distal and proximal end portions of the tubular section;

a longitudinal entrance channel extending along the length of each lumen and projecting outwardly from each lumen to define an entry into each lumen from the exterior of the tubular section, the entrance channels being configured to allow entry therein of fluids while substantially preventing entry of debris or living tissue from the body; and a plurality of spaced, transverse holes extending through the tubular section to couple the internal passageway with the region surrounding the tubular section, wherein each of the transverse holes intersects at least two of the channels and lumens.

2. A suction tube according to claim 1, wherein the spaced holes are positioned near the distal end portion of the tubular section.

3. A suction tube according to claim 2, wherein the transverse holes are formed in the elongate tube so that each transverse hole intersects the plurality of the channels and lumens; and the transverse holes are arranged in the elongate tube in at least two longitudinally extending sets such that each channel and lumen intersects with a single set of transverse holes.

4. A suction tube according to claim 1, further comprising connection means for coupling the proximal end of the tubular section to the suction source.

5. A suction tube according to claim 4, further comprising a flexible outflow tube for coupling the suction source and the tubular section, the outflow tube being connectable to the tubular section by the connection means.

6. A suction tube according to claim 5, wherein the outflow tube has a smooth external surface.

7. A suction tube according to claim 1, further comprising a bead or strip of radio-opaque material, the radio-opaque material being located at least in the distal end portion of the tubular section.

8. A suction tube according to claim 1, wherein the tubular section has a cross-sectional configuration selected from the group consisting of circular, oval, elliptical and polygonal.

9. A suction tube according to claim 1, wherein the internal longitudinal passageway has a cross-sectional configuration selected from the group consisting of circular, oval, elliptical and polygonal.

10. A suction tube according to claim 1, wherein the holes are positioned near the distal end portion of said tubular body.

11. A suction tube according to claim 10, wherein the holes are of substantially uniform size.

12. A suction tube according to claim 1, wherein the projecting portions are generally parallel to each other.

13. A suction tube according to claim 1, wherein the tubular section is made from a physiologically compatible elastomer.

14. A suction tube according to claim 13, wherein said elastomer is selected from a group consisting of a silicone polymer, a vinyl polymer, and a urethane polymer.

15. A suction tube according claim 1, wherein the transverse holes are arranged in at least two longitudinally extending and angularly offset lines along the tubular section; and, each line of the channels and lumens intersect a single line of transverse holes.

16. A suction tube according to claim 1, wherein the transverse holes are formed in both the elongate tubular section and in the projecting portions so that the transverse holes are open along the outer surfaces of the projecting portions and the transverse holes have a width greater than the width of the entrance channels.

17. A suction tube according to claim 16, wherein the projecting portions have substantially solid bodies.

18. A suction tube according to claim 1, wherein the projecting portions have substantially solid bodies.

19. A device for removing fluid from a cavity, viscus, or wound within a body that defines a suction site, the device comprising:

an elongate tube having a tubular wall defining an exterior surface and a longitudinal internal bore, a distal end and a proximal end, the proximal end defining a proximal end opening, the internal bore being coupled with the proximal end opening, the elongate tube being dimensioned to have sufficient length so that the proximal end is located distal of the suction site;

a plurality of elongate projection portions projecting outwardly from the exterior of the tube and extending from the distal end to the proximal end of the tube, wherein the projecting portions are configured and mutually circumferentially spaced so as to define a plurality of elongate lumens spaced apart about, and extending along, the tubular wall, the lumens spanning along the length of the tube from the distal end to the proximal end of the tube, each lumen having an entrance opening extending along the length of the lumen, the projecting portions further formed to define outer surfaces; and a plurality of apertures extending transversely through the tubular wall to couple the central bore with the region surrounding the tube, wherein each of the apertures is in fluid flow communication with at least two lumens.

20. A device according to claim 19, wherein the width of the entrance openings into the lumens is selected so as to readily permit liquid and gaseous fluids to enter said lumens while substantially preventing debris or living tissues from located within the suction site from entering the lumens.

21. A device according to claim 19 wherein the lumens extend generally parallel to each other along the length of the tube.

22. A device according to claim 19, wherein the apertures are formed both in the elongate tube and in the projecting portions so that the apertures are open along the outer surfaces of the projecting portions and the apertures have a width greater than the width of the entrance channels.

23. A device according to claim 22, wherein the projecting portions have substantially solid bodies.

24. A device according to claim 19, wherein the elongate tube has sufficient length to extend to the exterior of the body.

25. A device for removing fluids from the interior of a body, the device comprising:
- an elongate tube having a wall of predetermined thickness forming an outer surface and a central bore, a distal end and a proximal end, the elongate tube having a selected length such that when the distal end is located in the interior of the body, the proximal end is located outside of the body;
- a plurality of elongate external lumens formed in the wall and extending between the distal and proximal ends of the tube;
- a plurality of entrance channels, each associated with a respective one of the plurality of lumens, for coupling the lumen with the outer surface of the tube; and
- a plurality of apertures extending transversely through the wall to couple the central bore with the outer surface, each of the apertures being coupled with at least two lumens and channels associated therewith.

26. A device according to claim 25, wherein each of the channels are sized to permit liquid and gaseous fluids to enter the lumens while substantially preventing the entry of debris or living tissue from the body.

27. A device according to claim 25, wherein the apertures are formed in the wall of the elongate tube so as to intersect the lumens and to open along the outer surface of the tube, and to have a width greater than the width of the entrance channels.

28. A method of draining fluid from a suction site inside a living body comprising the steps of:
- positioning a suction tube inside the living body, the suction tube having: an elongate tubular section with an exterior surface and an interior surface that define in a longitudinal passageway, and that has distal and proximal end portions; a plurality of projecting portions extending away from the exterior surface of the tubular section, the projection portions being mutually circumferentially about the tubular section so as to form longitudinally extending lumens between adjacent projecting portions, and spanning between the distal and proximal ends of the tubular section so as to define longitudinal entrance channels that span along the length of each lumen that projects outwardly from each lumen to define an entry into the lumen, the entrance channels being configured to allow entry therein of fluids while substantially preventing the entry of the debris or living tissue from the body; and further having a plurality of spaced transverse holes extending through the distal end of the tube to couple the interior passageway with the regions surrounding the tubular section wherein each of the transverse holes intersects at least two of the channels and lumens, the positioning step further including the step of locating the tube so that the distal end of the tube is located at the suction site and the proximal end of the tube is spaced away from the suction site; and
- drawing a suction from the longitudinal passageway of the suction tube from the proximal end of the tube, the suction being sufficient to draw fluid located in the distal end portion of the longitudinal passageway of the suction tube toward the proximal end of the elongate tube, to draw fluid through the entrance channels, the lumens and the transverse holes into the longitudinal passageway, and to draw gaseous fluids through the portions of the tube located away from the suction site through the entrance channels, the lumens, and transverse holes to maintain a continuous pumping action through the elongate tube section.

29. A method of fluid drainage according to claim 28, further including the steps of:
- positioning the elongate tube section so that a portion of the proximal end of the elongate tube section is located outside of the body having the suction site; and
- drawing a sufficient suction through the proximal end of the tube so that atmospheric air is drawn into the proximal end of the elongate tube and through the transverse holes located at the suction site.

* * * * *